United States Patent [19]

Jaremus

[11] 4,219,330
[45] Aug. 26, 1980

[54] DENTAL HANDPIECE AND ROTOR CARTRIDGE REPLACEMENT ASSEMBLY THEREFOR

[75] Inventor: Boubene M. Jaremus, Barrington, Ill.

[73] Assignee: American Hospital Supply Corporation, Evanston, Ill.

[21] Appl. No.: 944,171

[22] Filed: Sep. 20, 1978

[51] Int. Cl.² ............................................. A61C 1/08
[52] U.S. Cl. .................................... 433/126; 433/132
[58] Field of Search ........................... 32/27; 415/503; 433/126, 132, 117

[56] References Cited

U.S. PATENT DOCUMENTS

| | | | |
|---|---|---|---|
| 2,945,299 | 7/1960 | Fritz | 32/27 |
| 3,298,103 | 1/1967 | Maurer | 32/27 |
| 3,325,899 | 6/1967 | Staunt | 32/27 |
| 3,376,084 | 4/1968 | McKee | 32/27 |
| 3,888,008 | 6/1975 | Lake et al. | 32/27 |
| 4,071,954 | 2/1978 | Eibofner | 32/27 |

Primary Examiner—Louis G. Mancene
Assistant Examiner—John J. Wilson
Attorney, Agent, or Firm—Tilton, Fallon, Lungmus & Chestnut

[57] ABSTRACT

A dental handpiece equipped with an improved rotor cartridge and, in particular, a rotor cartridge replacement assembly for such a handpiece. The rotor cartridge takes the form of a subassembly of a rotor, bearings for the rotor, resilient rings supporting the bearings, and a plastic cup member extending about the lower bearing assembly and the resilient support ring therefor. In addition to the rotor cartridge, the replacement assembly may also include a threaded cap and a support tool which not only holds the cap and cartridge together but also may be used for inserting and securing the parts in place within the head housing of a dental handpiece.

20 Claims, 4 Drawing Figures

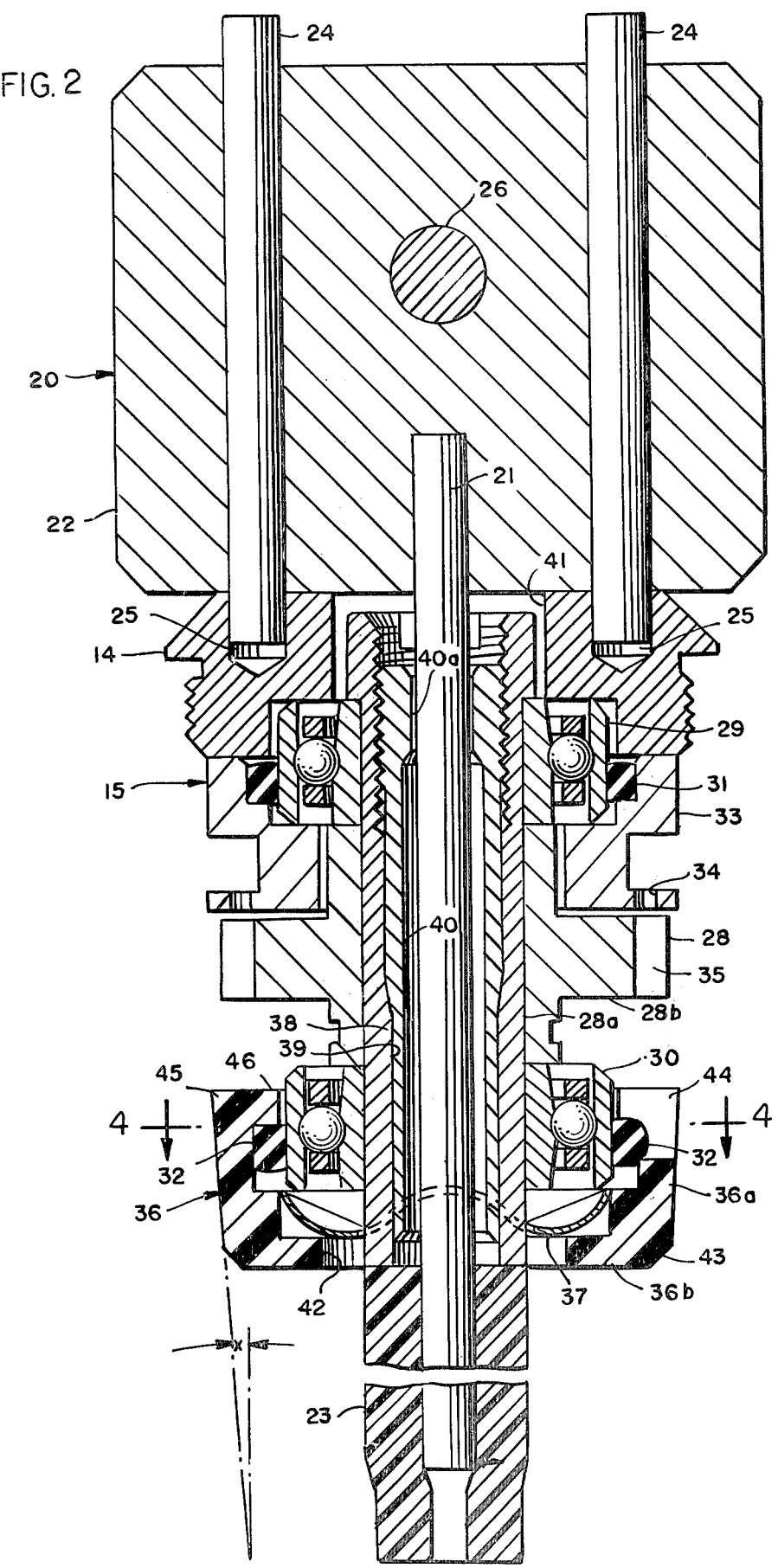

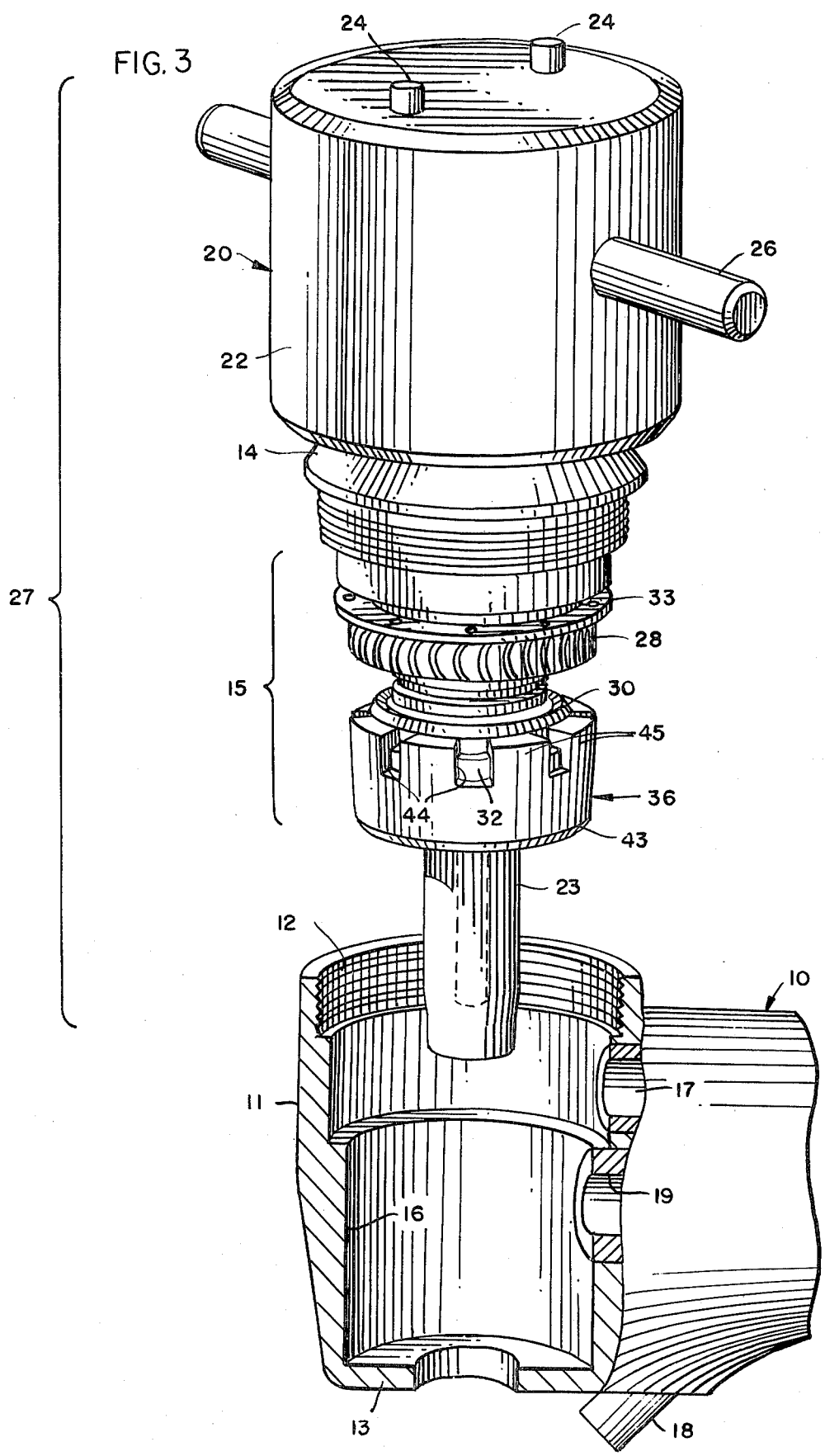

DENTAL HANDPIECE AND ROTOR CARTRIDGE REPLACEMENT ASSEMBLY THEREFOR

BACKGROUND AND SUMMARY

The high speed operation of conventional air driven contra angle handpieces tends to accelerate bearing wear and gives rise to a need for bearing replacement at periodic intervals. Because of the small size of the parts and the precision with which they must be fitted together, bearing replacement for such dental handpieces is still commonly a factory rebuilding operation requiring the skill of highly trained workers. Such reconstruction is, unfortunately, relatively expensive and time consuming. Since downtime for a given handpiece depends on the availability of trained workers capable of carrying out such reconstruction, and since the number of such skilled workers is limited, it is not uncommon for dentists to wait days or even weeks for factory rebuilding of their handpieces.

Efforts have been made to simplify the rebuilding of such handpieces so that dentists might perform the work themselves, but such efforts have been only marginally successful. A common approach has been to form a rigid cartridge consisting essentially of a rotor (which includes a bur tube), a pair of bearing assemblies, and a shell which securely locks the bearings in alignment and at the proper pre-load. When replacement becomes necessary, the dentist removes the cap from the handpiece housing, withdraws the old cartridge, and replaces it with a new self-contained cartridge unit. U.S. Pat. Nos. disclosing such a cartridge arrangement are 3,255,527, 2,945,299, 3,324,553, 3,084,439, and 3,411,212.

Among the disadvantages of such a rigid cartridge system are the increased bulk caused by the secondary shell which locks the bearings and other components in proper operating relation and the requirement that the cartridge be manufactured to extremely close tolerances so that it will fit precisely in existing housings. The result is that a system utilizing a rigid cartridge construction to permit field replacement is achieved only at relatively high cost and with some disadvantages of increased bulk and weight.

To avoid the disadvantages of rigid cartridge systems, some manufacturers have marketed replacement rotor subassemblies in which all of the replacement parts are carried by spindles which only support the parts until they are mounted within a handpiece housing. While such subassemblies are sometimes called "cartridges", they differ from other cartridge systems because, among other things, no shells are utilized for rigidly securing the parts together in fixed relation. The bulk and weight arising from the use of a cartridge shell are therefore avoided; however, such a system does increase the possibility that some of the components of the replacement assembly, such as the resilient support rings for the bearings, may be shifted out of position, become damaged (the resilient rings may be pinched or cut by malassembly), or fail to seat properly within a handpiece housing unless considerable care is exercised in making the replacement.

An object of this invention is therefore to overcome the aforementioned disadvantages of prior constructions. Specifically, it is an object to provide a system which permits quick and simple field reconstruction of a worn handpiece at relatively low cost and with virtually no risk of misalignment or faulty assembly of the parts.

In the system of the present invention, no rigid cartridge is used. The combination of parts which might for convenience be referred to as a "cartridge" is really a subassembly frictionally held together by resilient rings which serve the ultimate purpose of cushioning the parts and reducing sound development in a fully assembled handpiece. Such resilient rings are protected against displacement during field replacement by protective surrounding elements and by the remaining components of the rotor cartridge replacement assembly. More specifically, the lower bearing assembly and the resilient ring which encircles it are surrounded by a flexible plastic cup which is adapted to seat within the lower end of the head housing of a dental handpiece. The flexible side wall of the plastic cup has a slight taper which not only facilitates insertion into the handpiece housing but also insures a secure interfit between the cup and housing. In other words, the wall of the plastic cup is capable of flexing inwardly to a limited extent to conform to the inside dimensions of the head housing.

Such flexure of the cup's side wall is facilitated by a multiplicity of notches which are spaced circumferentially about the rim of the cup and which define a multiplicity of spring fingers formed integrally with the cup's side wall. The spring fingers surround and retain the resilient support ring for the lower bearing assembly and, especially when the rotor cartridge or subassembly is mounted within the housing of a handpiece, such fingers exert a compressive force on the ring which serves to hold the cup, ring, and lower bearing assembly (along with other elements such as, for example, a wave washer) frictionally together. The security of such frictional engagement is increased by reason of the fact that the resilient ring tends to bulge or expand slightly into the notches of the cup, thereby reducing the possibility of independent relative movement of the parts.

In addition to the above advantages, the flexible plastic cup also serves as a non-metallic spacer between the lower bearing assembly and the handpiece housing and, along with the resilient support ring, further reduces the transmission of sound generated during operation of the high speed handpiece.

The rotor cartridge or subassembly is part of a larger assembly which includes a housing cap and a support tool for holding the parts together during shipment and storage and for inserting and securing such parts in place when handpiece reconstruction is required. The tool includes an enlarged upper retaining element in the form of a wrench which is keyed to the threaded handpiece cap so that, following insertion of the rotor subassembly into the cavity of the handpiece housing, the wrench may be rotated to secure the threaded cap in place. The tool also includes a spindle which extends through both the cap and the rotor cartridge, and a lower retaining element in the form of a sleeve which is located at the lower end of the spindle and which holds the cap and cartridge in place upon that spindle until such time as removal is desired. One of the retaining elements, either the wrench or sleeve, is removable from the spindle to permit extraction of the spindle after the replacement rotor assembly has been secured within the handpiece housing. In the embodiment disclosed, the removable member is the lower retaining element which takes the form of a plastic sleeve frictionally secured to the lower end of the spindle.

Other features, objects, and advantages of the system of this invention will become apparent from the specification and drawings.

DRAWINGS

FIG. 2 is an enlarged vertical sectional view of a complete rotor cartridge replacement assembly.

FIG. 3 is an enlarged perspective view illustrating the relationship between the rotor cartridge replacement assembly and the head housing of a dental handpiece.

DESCRIPTION OF PREFERRED EMBODIMENT

Figure 1:
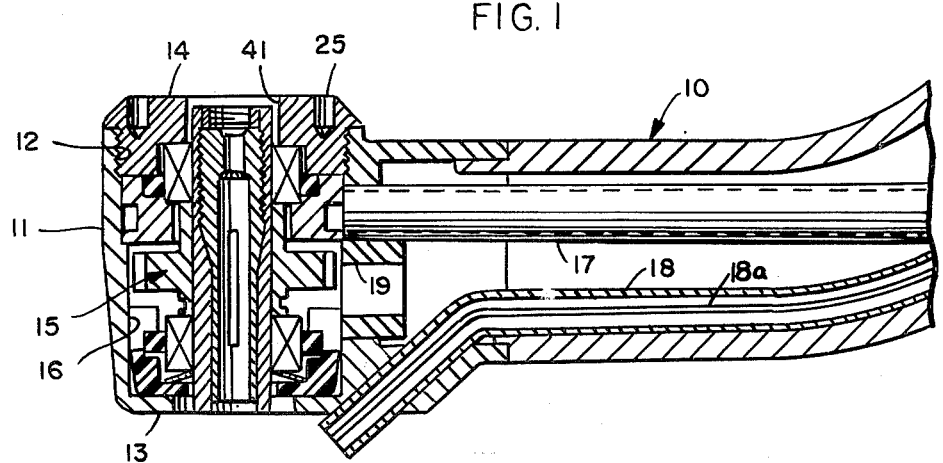
FIG. 1 is a fragmentary vertical sectional view showing the head housing of a contra angle handpiece equipped with the rotor assembly of this invention.

Referring to FIG. 1, the numeral 10 designates the handle of a contra angle air-driven dental handpiece, the handle terminating in a head housing 11 having an enlarged threaded opening 12 at its upper end and a centrally apertured bottom wall 13 at its lower end. An externally threaded cap 14 is secured to the upper end of the housing to retain the rotor "cartridge" 15 within the cavity 16 of the housing. The term "cartridge" will be used herein as a matter of convenience although it will become apparent as the specification proceeds that the parts so designated do not constitute a rigid unitary cartridge but are instead a subassembly of the basic components of the handpiece which are held securely together in operative relationship only when they are fully mounted in a handpiece as shown in FIG. 1.

The handle of the handpiece includes a tube 17 for delivering drive air to the operating mechanism. Tube 18 carries chip-blowing air and 18a delivers water to the work area for cooling the bur and tooth during a cutting operation and for clearing chips from the work area. Exhaust air discharged from the turbine passes into the handle through exhaust port 19.

Figure 4:
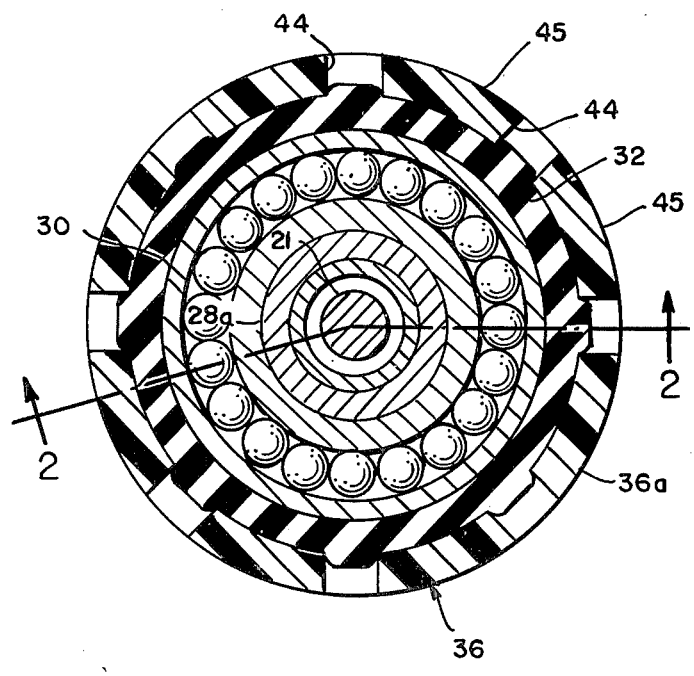
FIG. 4 is an enlarged horizontal sectional view taken along line 4—4 of FIG. 2.

FIGS. 3 and 4 depict the rotor subassembly or cartridge removed from head housing 11 and carried by a supporting tool 20 along with handpiece cap 14. The tool includes a spindle 21 which extends axially through all of the components of the cartridge 15 and through end cap 14, an upper retaining element 22, and a lower retaining element 23. One of the retaining elements is secured to the spindle while the other is only frictionally held in place and may be removed therefrom; in the preferred embodiment illustrated, the lower element 23, which takes the form of a resilient plastic sleeve, is removably fitted upon the lower end of the spindle while the upper retaining element 22, which takes the form of an enlarged cylindrical knob, is more permanently secured to the spindle's upper end. The cylindrical knob 22 has a diameter greater than cap 14 and includes two (or more) eccentrically located pins 24 which extend beyond the knob and which are positioned to be received within sockets 25 in cap 14. The pins therefore key the cap 14 and the supporting tool 20 against independent relative rotation so that the tool may be used as a torsion wrench to screw cap 14 into place. A transverse torque bar 26 may extend through the cylindrical body 22 and project radially beyond that body to assist a user in applying the required force in tightening (or loosening) a handpiece cap 14. It will be noted that pins 24 project from the upper surface of cylindrical body 22 (FIG. 3) as well as downwardly into the sockets of cap 14; hence, the tool may be used as a wrench to remove the old cap from an existing handpiece requiring replacement of its operating mechanism without disturbing the rotor subassembly supported on the opposite side of the wrench.

The supporting tool 20, cap 14, and cartridge or rotor subassembly 15 together form a unitary rotor cartridge replacement assembly designated generally by the numeral 27 in FIG. 3. The assembly 27 represents all that is required to permit a user to replace the operating mechanism of an airdriven dental handpiece. By inverting the assembly, the exposed stub ends of pins 24 are used to engage and remove the existing cap from a handpiece requiring rotor replacement. After the worn or damaged mechanism is removed from head housing 11, the new rotor cartridge or subassembly 15 is inserted into the cavity 16 of the housing in the manner depicted in FIG. 3. The new cap 14 is screwed into place using tool 20 as a wrench. Thereafter, the resilient sleeve 23 is removed from the lower end of the spindle (an action which may be achieved simply by lifting the tool by means of torque bar 26), and the tool is removed from the rebuilt handpiece.

Referring in particular to FIGS. 2 and 3, the rotor cartridge or subassembly 15 comprises a turbine rotor 28, upper and lower bearing assemblies 29 and 30, resilient support rings 31 and 32 surrounding the outer races of the upper and lower ball bearing assemblies, respectively, a stator ring 33 having apertures 34 for directing drive air axially against the vanes 35 of the turbine, a cup-shaped member 36 surrounding the lower bearing assembly 30 and a resilient support ring 32, and a wave spring 37 for exerting an axial pre-load from the outer race of the lower bearing assembly and for urging the cup member 36 into properly seated condition within the cavity of the handpiece's head housing. Rotor 28 includes a bur tube 28a which extends through a bore in turbine 28b, it being understood that, if desired, the turbine and bur tube may be integrally formed. A suitable chuck 38 extends through the axial bore 39 of the bur tube and is threadedly adjustable within that bore for the purpose of clamping or releasing a dental bur (not shown) which in normal handpiece operation would be mounted within the bore 40 of the chuck. Bore 40, including bore portion 40a, extends completely through the chuck and that bore, combined with the upper end of bur tube bore 39, together define an opening which extends axially and completely through rotor cartridge 15. Bore portion 40a is non-circular (square) in cross section to receive the non-circular shaft of a suitable wrench (not shown) used to apply torsional force to the chuck during tightening or loosening of the chuck.

Cap 14 is similarly provided with an opening 41 coaxial with opening 40. As shown in FIG. 2, spindle 21 may therefore extend axially through the central opening 41 and the openings 39 and 40 of bur tube 28a and chuck 38, respectively. The spindle is dimensioned to be loosely received in the passage or opening extending through the cartridge 15 and superimposed cap 14, such parts being retained on the spindle because of the cylindrical knob or body 22 which engages the top surface of the cap and the retaining sleeve 23 which engages the bottom surface of rotor 28.

In the particular form of turbine illustrated in the drawings, air passes in a generally axial direction through the turbine blades, in contrast to a construction in which air impinges on the blades in a tangential or radial direction. The former requires a stator, as represented by stator ring 33, whereas in the latter cases, as in a Pelton wheel turbine, a stator may be unnecessary. It is to be understood, therefore, that a stator as such is not an essential element of the rotor cartridge subassembly unless an axial-flow of turbine of the general type depicted in the drawings is utilized. On the other hand, some means must be provided for retaining the upper resilient support ring 31 and, as shown in the drawings (FIG. 2), ring 33 also performs that function.

Cup-shaped member 36 is formed of a tough flexible plastic material such as nylon, although it is believed apparent that other materials having similar properties may also be used. The cup includes a side wall 36a and an integral end or bottom wall 36b, the latter being provided with a central aperture 42 to accommodate the lower end of rotor 28 and to permit the escape of cooling (and lubricating) air passing through the lower bearing assembly 30 and wave washer 37. The outer corner of the cup is beveled or rounded at 43 (FIG. 2) and the side wall 36a has an outer surface which is slightly frusto conical in shape, sloping gradually upwardly and outwardly at an angle x within the range of about 1 to 5 degrees from the vertical.

The cavity of the cup retains the wave washer or spring 37, the lower bearing assembly 30, and the resilient support ring 32. As shown most clearly in FIGS. 3 and 4, the sloping side wall of the cup is provided with a plurality of circumferentially-spaced notches which extend downwardly from the top of the cup to a level intermediate the upper and lower limits of side wall 36a. Such notches thereby define a plurality of upstanding flexible fingers 45 formed as integral parts of side wall 36a. Resilient ring 32 is squeezed or tightly held between such fingers and the outer race of bearing assembly 30 with the result that portions of the ring expand or are forced limited distances into the notches between the fingers (FIG. 4). Such limited expansion of the resilient ring into the notches assists in holding the ring in place, that is, in preventing relative movement between the resilient support ring 32 and the cup 36.

Each finger 45 of the cup is provided with an inwardly projecting lip or flange 46 at its upper end for the purpose of retaining the resilient support ring 32 against upward axial displacement with respect to the cup. It will be observed, however, that the inner surfaces of the lips define an opening appreciably larger than the inside diameter of resilient support ring 32 (or the outside diameter of bearing assembly 30) so that no direct contact between the cup and bearing assembly occurs.

As part of the rotor cartridge 15, the tapered cup 36 performs important functions in helping to guide the lower end of a rotor cartridge replacement assembly into place within the cavity of the head housing of a dental handpiece, of protecting the resilient support ring 32 and spring washer 37 against displacement during such an insertion step, and of reducing the transmission of sound and virbration from the lower bearing assembly to the head housing during handpiece operation. The cup also serves to protect the lower bearing assembly against forces which might otherwise cause slight misalignment of the upper and lower bearing assemblies, since fingers 45 are capable of flexing slightly to accommodate such differences and absorb such forces. In addition, the slightly frusto conical configuration of the cup's outer surface permits greater dimensional tolerances during manufacture while at the same time insuring that the cup will fit firmly and properly within the head cavity of a dental handpiece, thereby permitting a reduction in manufacturing and selling costs without reducing quality of construction or performance.

While in the foregoing I have disclosed a preferred embodiment of the invention in considerable detail for purposes of illustration, it will be understood that many of these details may be varied without departing from the spirit and scope of the invention.

I claim:

1. A multi-component rotor subassembly for dental handpieces, said subassembly having an axial opening therethrough for slidably receiving a spindle of a supporting tool and including as components of said subassembly a rotor, at least one rotor bearing assembly and resilient support ring therefor, and a plastic cup member; said cup member having a flexible and gradually tapered side wall and a centrally apertured end wall; said bearing assembly being received in said cup member, and said resilient support ring being frictionally secured between said bearing assembly and said flexible side wall; said side wall being provided with a plurality of circumferentially-spaced notches defining therebetween a plurality of flexible fingers engaging said resilient bearing support ring.

2. The subassembly of claim 1 in which each of said fingers is provided with a radially inwardly extending lip at the free end thereof, said lips engaging said resilient ring.

3. The subassembly of claim 1 in which a compression spring is disposed within said cup member between said end wall and said bearing assembly.

4. The subassembly of claims 1, 2 or 3 in which said cup member is formed of flexible plastic material.

5. A multi-component rotor replacement subassembly for dental handpieces; said subassembly having an axial opening therethrough for slidably receiving a spindle of a supporting tool and including as components of said subassembly a rotor comprising a bur tube and turbine, a pair of ball bearing assemblies mounted on said rotor, a pair of resilient support rings extending about said bearing assemblies, a stator, and a cup member having a side wall and a centrally-apertured end wall; said side wall having an outer surface tapering gradually in the direction of said end wall; said cup member receiving one of said bearing assemblies and having one of said resilient rings disposed in a state of limited compression between said one bearing assembly and said side wall; said side wall being flexible for yieldable engagement with the inside surface of a handpiece housing into which said replacement subassembly is inserted; said side wall of said cup member being provided with a plurality of circumferentially-spaced notches defining therebetween a plurality of flexible fingers integral with the side wall of said cup member; said one resilient ring being directly and forcefully engaged by said fingers and protruding slightly into the notches between said fingers.

6. The subcombination of claim 5 in which a compression spring is disposed within said cup between said end wall and said one bearing assembly.

7. The subcombination of claims 5 or 6 in which said cup member is integrally formed of flexible plastic material.

8. The subassembly of claim 5 in which said stator is annular in configuration and extends about the other of said bearing assemblies; and said other of said resilient rings being interposed between said stator ring and said other bearing assembly.

9. A rotor cartridge replacement assembly for a contra angle dental handpiece, comprising a supporting tool having a spindle and a pair of retaining members; a multi-component rotor subassembly having an axial opening extending therethrough and slidably receiving said spindle; one of said components being a cup member formed of flexible plastic material and disposed at one end of said subassembly; a centrally-apertured disc-shaped threaded cap carried by said spindle at the opposite end of said subassembly; said cap and subassembly being disposed between and engaged by said retaining members; one of said retaining members being removable from said spindle for withdrawing said spindle from said cap and said subassembly after the same has been mounted within a dental handpiece.

10. The assembly of claim 9 in which said one of said retaining members engages said subassembly; said other of said retaining members being in engagement with said cap; and means provided by said other retaining member and said cap for locking the same against independent relative rotation.

11. The assembly of claim 10 in which said means includes locking pins extending from said other of said retaining members and received within openings in said other of said retaining members.

12. The assembly of claim 11 in which said pins also project from said other of said retaining members in a direction away from said cap to provide lugs for engaging and removing the cap of a dental handpiece.

13. The assembly of claim 9 in which said rotor subassembly also includes as components thereof a rotor, a spaced pair of rotor bearing assemblies, a pair of resilient support rings disposed about said bearing assemblies, and a stator ring; said plastic cup member having a flexible side wall and a bottom wall and receiving therein one of said bearing assemblies; and one of said resilient support rings being disposed between said one bearing assembly and said flexible side wall within said cup member.

14. The assembly of claim 13 in which said flexible side wall of said cup member has a frusto conical outer surface tapering gradually in a direction away from said cap.

15. The assembly of claim 14 in which said side wall of said cup member is provided with a plurality of circumferentially-spaced notches defining therebetween a plurality of flexible fingers; said one of said resilient support rings being forceably engaged by said flexible fingers and protruding to a limited extent into the notches between said fingers.

16. A contra angle dental handpiece having a handle and a generally cylindrical head housing, said housing having an enlarged threaded opening at one end and a centrally-apertured end wall at the other, a cap threadedly secured within said opening, and a multi-component rotor cartridge coaxially disposed within said housing, wherein the improvement comprises said cartridge including a rotor, a pair of rotor bearing assemblies, a pair of resilient support rings for said bearing assemblies, and a cup member; said cup member having a flexible annular side wall and a centrally-apertured end wall; one of said bearing assemblies being disposed within said cup member with one of said resilient support rings tightly fitted between said one bearing assembly and said flexible side wall; said flexible side wall firmly engaging the inner surface of said head housing; said side wall of said cup-shaped member being provided with a plurality of circumferentially-spaced notches defining therebetween a plurality of flexible fingers engaging both said one resilient support ring and said inner surface of said head housing.

17. The handpiece of claim 16 in which said side wall of said cup member has a frusto-conical outer surface tapering gradually towards said end wall.

18. The handpiece of claim 17 in which said taper falls within the range of about 1 to 5 degrees from the axis of said rotor cartridge.

19. The handpiece of claim 16 in which said one resilient support ring is compressed between said one bearing assembly and said side wall of said cup member and protrudes into said notches between said fingers.

20. The handpiece of claims 16, 17, or 19 in which said cup member is formed of flexible plastic material.

* * * * *